United States Patent
Haider et al.

(10) Patent No.: US 6,346,079 B1
(45) Date of Patent: Feb. 12, 2002

(54) METHOD AND APPARATUS FOR ADAPTIVE FRAME-RATE ADJUSTMENT IN ULTRASOUND IMAGING SYSTEM

(75) Inventors: Bruno Hans Haider, Ballston Lake; Kenneth Wayne Rigby, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/577,849

(22) Filed: May 25, 2000

(51) Int. Cl.[7] ............................................. A61B 08/00
(52) U.S. Cl. ...................................... 600/443; 600/447
(58) Field of Search .............................. 600/454, 453, 600/444, 443, 447, 448, 449

(56) References Cited

U.S. PATENT DOCUMENTS 5,904,653 A * 5/1999 Hatfiled et al. ............. 600/454
6,210,332 B1 * 3/2001 Chiao et al. ................ 600/443

* cited by examiner

*Primary Examiner*—Marvin M. Lateef
*Assistant Examiner*—Maulin Patel
(74) *Attorney, Agent, or Firm*—Jill M. Breedlove; Christian G. Cabou

(57) ABSTRACT

A method and an apparatus for dynamically optimizing the frame rate as a function of an estimate of the target motion. First, the target motion is estimated, and then this estimate is used to control the number of firings per frame and/or the degree of frame-averaging. Preferably, the motion of the target is estimated by measuring pixel brightness variations on a frame-to-frame, region-to-region or line-to-line basis. Then the degree of frame-averaging is adjusted as a function of the motion estimate. Alternatively, target motion can be estimated by calculating the Doppler signal. Other imaging parameters, such as number of transmit firings per frame, size of the transmit aperture, and transmit excitation frequency, can be adjusted as a function of estimated target motion.

26 Claims, 3 Drawing Sheets

METHOD AND APPARATUS FOR ADAPTIVE FRAME-RATE ADJUSTMENT IN ULTRASOUND IMAGING SYSTEM

FIELD OF THE INVENTION

This invention generally relates to ultrasound imaging for the purpose of medical diagnosis. In particular, the invention relates to methods for imaging tissue and blood flow by detecting ultrasonic echoes reflected from a scanned region of interest in a human body.

BACKGROUND OF THE INVENTION

A conventional ultrasound image is composed of multiple image scan lines. A single scan line (or a small, localized group of scan lines) is acquired by transmitting focused ultrasound energy at a point in the region of interest and then receiving the reflected energy over time. The focused transmit energy is referred to as a transmit beam. During the time after transmit, one or more receive beamformers coherently sum the energy received by each channel, using dynamically changing phase rotation or time delays to produce peak sensitivity along the desired scan lines at ranges proportional to the elapsed time. The resulting focused sensitivity pattern is referred to as a receive beam. A scan line's resolution results from the directivity of the associated transmit and receive beam pair.

In a typical ultrasound imaging system, the outputs of the beamformer channels are coherently summed and envelope-detected to form a respective intensity value for each sample volume in the object region or volume of interest. These intensity values are log-compressed, scan-converted and then displayed as pixels in an image frame of the anatomy being scanned. Successive image frames are typically averaged prior to scan conversion with the goal of reducing electronic and speckle noise.

The design of medical ultrasonic imaging equipment requires a careful compromise between image quality and frame rate. Some techniques are available which can improve frame rate without significantly degrading image quality. For example, state-of-the-art ultrasound imagers allow for the simultaneous acquisition of multiple receive scan lines for a single transmit firing or apply advanced interpolation schemes which reduce the required number of receive scan lines. However, even after exploiting these methods there is still a need to improve frame rate without significantly degrading image quality.

To achieve the desired image quality, the ultrasound imaging system compromises the frame rate in two ways. First, a large number of transmit focal points are used to obtain good spatial resolution. The best resolution can only be achieved when the transmit beam is tightly focused, that is, when the transmit aperture operates at a low f-number. However, a tight transmit focus results in a short depth of field and thus requires a large number of focal points to maintain the transmit focus over the region of interest.

The second frame rate compromise (at least to the perceived frame rate) occurs in the frame-averaging or image persistence processing. This processing applies a FIR or IIR filter to successive acoustic frames at each image pixel to reduce electronic and speckle noise. If the image is exactly stationary, then such processing reduces the electronic noise while preserving the desired acoustic image. Because electronic noise is reduced, the depth to which anatomy can be perceived is increased. If the target is moving slightly with respect to the transducer, then a beneficial speckle averaging also occurs. The speckle structure is typically on a finer scale than the anatomical features. Thus, with small target motions, frame-averaging reduces the speckle variation while retaining the anatomical structures. Larger target motions, however, blur the anatomical structures and reduce the diagnostic usefulness of the frame-averaged image.

Conventional ultrasound imaging systems provide a selection of "presets" which control the image quality to frame rate compromise on an application-specific basis. Additionally, the user has the option of modifying these presets by changing imaging parameters such as number of transmit focal points, displayed image size, scan line density, degree of frame-averaging and so on. However, once the system is configured, it remains in this operating condition until the user makes another parameter adjustment.

A low imaging frame rate is objectionable when the displayed structures move rapidly within the image. However, the importance of a high frame rate is reduced when the target is stationary. Typically, the sonographer moves the transducer in a search phase until the best view of the region of interest is found. This region is then examined in an evaluation phase for some type of lesion or other abnormality. During the search phase, high frame rate is often more important than image quality, while image quality is more relevant than frame rate in the evaluation phase. There is a need for a method of adaptively adjusting the frame rate in accordance with this understanding.

SUMMARY OF THE INVENTION

The invention disclosed herein approaches the image quality and frame rate compromise in a different way. It is based on the recognition that while image quality and frame rate are both important, they are often not required simultaneously. During the search phase, when the transducer is moving and large target motions result, high frame rate is more important and image quality can be somewhat reduced. In the search mode the user cannot take advantage of an optimal image quality because the target moves too rapidly. During the evaluation phase, when the target is stationary or moving slowly, the user concentrates on the image details and requires optimal image quality. High frame rate is less important since no motion artifacts are introduced. The invention disclosed herein dynamically optimizes the frame rate using an estimate of the target motion.

The frame rate depends upon the number of transmit firings in an image frame, i.e., the number of transmit focal zones in each scan line and the number of scan lines in the image frame. By reducing the number of firings, the frame rate is increased. Additionally, the frame rate perceived by the operator depends on the degree of frame-averaging, or image persistence. The dynamic frame rate adjustment in accordance with the preferred embodiment comprises two steps. First, the target motion is estimated, and then this estimate is used to control the number of transmit firings per frame and/or the degree of frame-averaging.

The motion estimation can be as complex as a two-dimensional cross-correlation between frames. However, the method presented here requires only a low accuracy in the estimate of the magnitude of the motion and does not require any information about the direction of the motion. Therefore in accordance with the most preferred embodiments of the invention, the motion is estimated by measuring pixel brightness variations. This estimate can be calculated using all the pixels in the image frame (frame-to-frame estimation), using pixels within a selected region with the image frame (region-to-region estimation), or between individual scan lines within the image frame (line-to-line estimation). Alternatively, motion can be detected by measuring a Doppler signal.

In accordance with one preferred embodiment of the invention, the degree of frame-averaging is adjusted as a function of the estimated target motion during operation of the imaging system. In accordance with another preferred embodiment, the number of transmit firings per frame is adjusted as a function of estimated target motion. Other imaging parameters, such as the size of the transmit aperture and the transmit excitation frequency can also be adjusted as a function of estimated target motion.

The user is presented with an image that smoothly tracks the target motion yet provides optimal image quality when the target is stationary or nearly stationary.

DETAILED DESCRIPTION OF THE PREFERRED EMBODIMENTS

Figure 1:
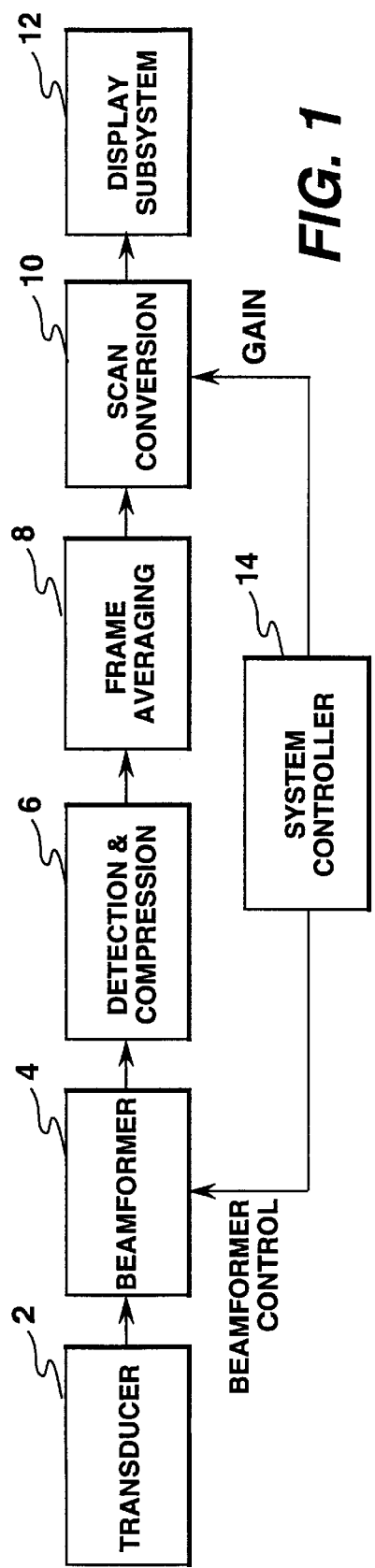
FIG. 1 is a block diagram generally showing a conventional ultrasound imaging system.

Referring to FIG. 1, a typical real-time digital ultrasound imaging system comprises, in sequence, a transducer array 2, a beamformer 4, a detection and compression signal processor 6, a frame-averaging filter 8, a scan converter 10 and a display subsystem 12. The transducer array 2 comprises a multiplicity of transducer elements which are activated by a transmitter in beamformer 4 to transmit an ultrasound beam focused at a transmit focal position. The returned acoustic signals are detected by the transducer elements and then dynamically focused at successive ranges along a scan line by a receiver in beamformer 4 to form a receive vector of raw acoustic data samples. The beamformer output data for each scan line is passed through a detection and compression signal processor 6, which typically performs envelope detection and logarithmic compression. The resulting log-compressed pixel intensity values are then typically frame-averaged in a frame-averaging filter 8 to reduce electronic and speckle noise and then interpolated in a scan converter 10. Alternatively, the log-compressed pixel intensity data can be interpolated first and then frame-averaged. The pixel intensity data is output to the display subsystem 12, which typically comprises a video processor for mapping the pixel intensity data to grayscale imaging data and a display monitor for displaying the grayscale imaging data.

The operation of the system depicted in FIG. 1 is controlled by a system controller 14. In particular, the system controller provides beamforming parameters to the beamformer 4. The system controller 14 also provides a frame-averaging gain for determining the filter coefficients to be used by the frame-averaging filter 8, thereby setting the persistence level of the frame-averaging filter. Although FIG. 1 depicts separate paths for the communications to and from the system controller 14, it will be readily appreciated that these communications may take place over a common channel or system bus.

Figure 2:
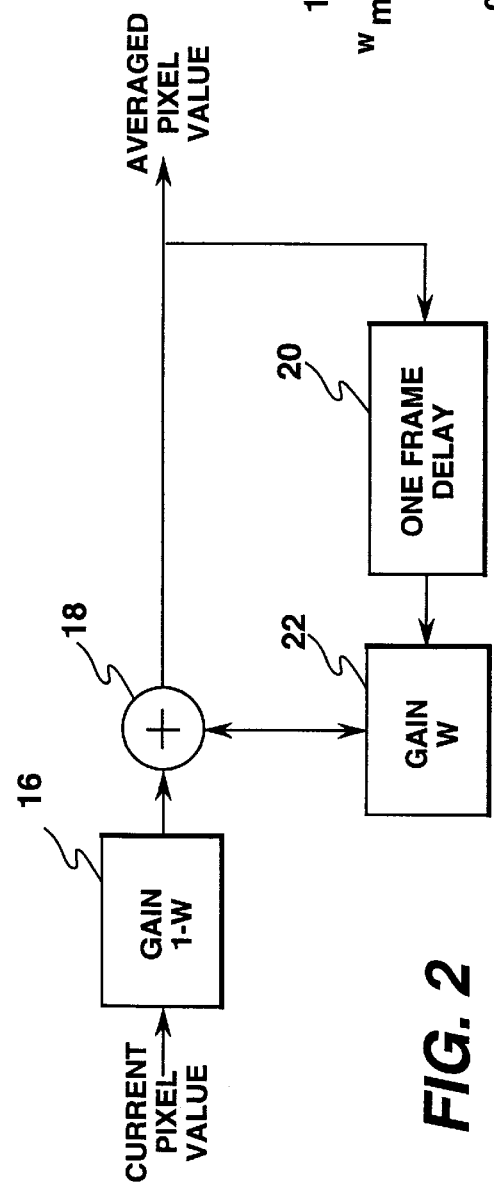
FIG. 2 is a flowchart depicting a conventional frame-averaging function.

In a conventional system, frame-averaging typically involves forming a weighted average of the pixel intensity values of the current image frame and the pixel intensity values of the previous averaged image frame. This operation is shown for one pixel in FIG. 2. The averaged pixel intensity value for the i-th frame is delayed by the inverse of the frame rate (block 20 in FIG. 2) and multiplied by a gain w (block 22), where $0 < w \leq w_{max} < 1$. At the same time, the current pixel intensity value for the corresponding pixel of the (i+1)-th frame is multiplied by a gain of (1−w) (block 16). The resulting values are then summed in summer 18 to produce the averaged pixel intensity value for the (i+1)-th frame, and so forth.

Figure 3:
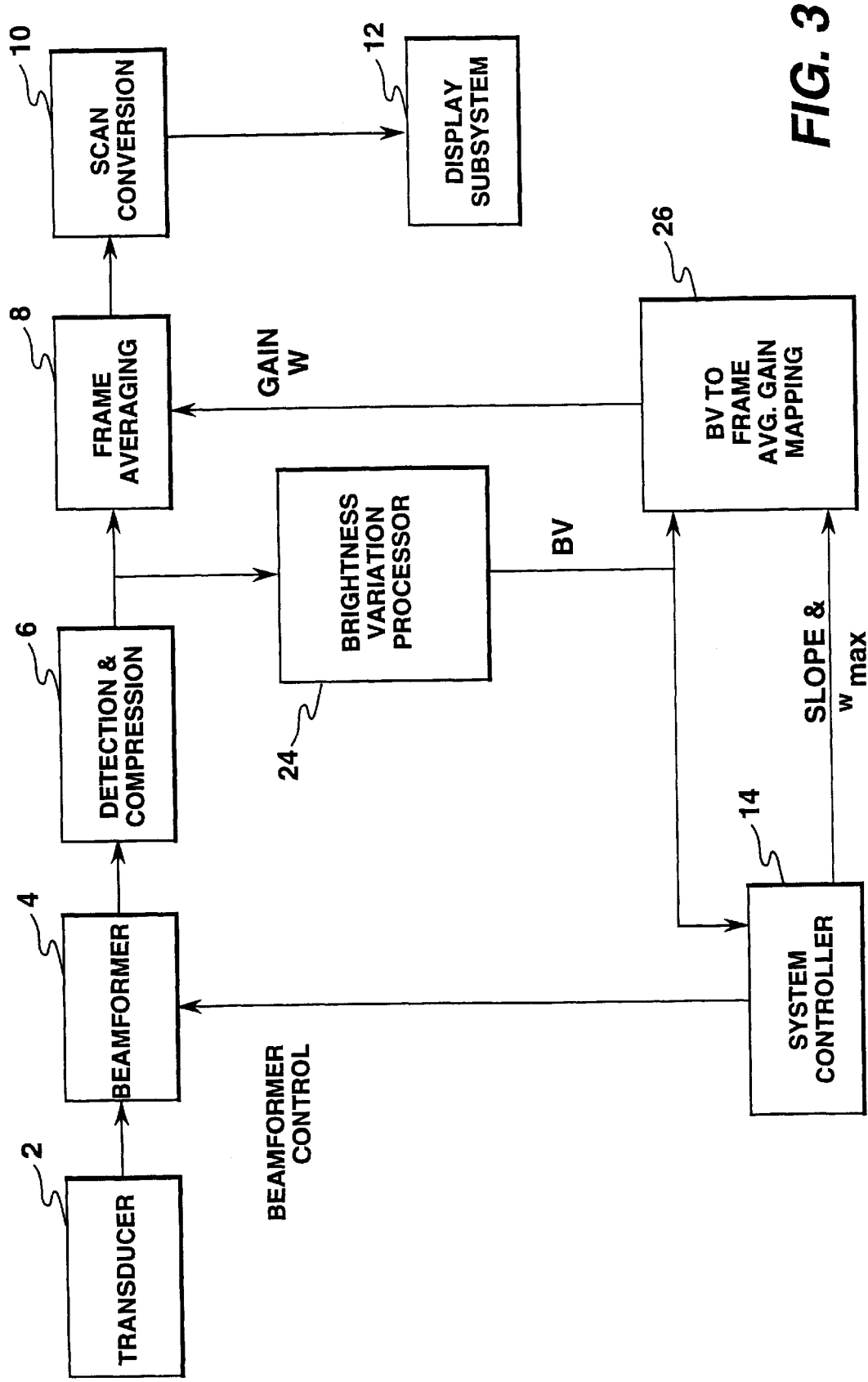
FIG. 3 is a block diagram showing one preferred embodiment of the invention in which the frame-averaging gain is adjusted as a function of pixel brightness variation.
Figure 5:
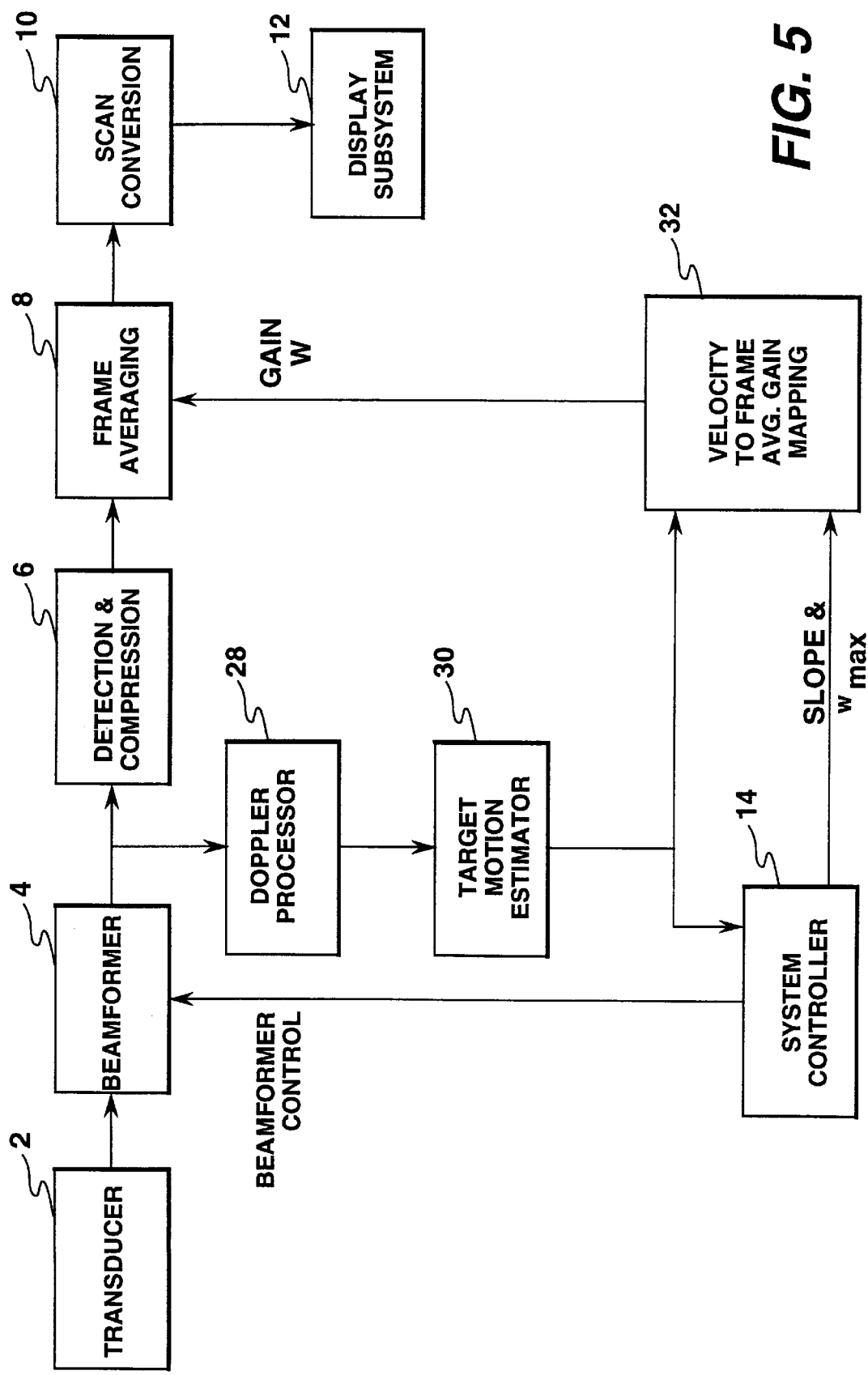
FIG. 5 is a block diagram showing another preferred embodiment of the invention in which the frame-averaging gain is adjusted as a function of the Doppler signal.

A preferred embodiment of the invention is shown in FIG. 3. The log-compressed pixel intensity data is output to a pixel brightness variation processor 24, which is programmed to estimate target motion by calculating the average pixel brightness variation over a set of corresponding pairs of pixels. The pixel brightness variation, BV, can be measured using the equation $$BV = \frac{\sum_{pixels} |p_{new} - p_{old}|^n}{N_{pixels}} \quad (1)$$

where $P_{new}$ and $P_{old}$ are the corresponding new and old pixel intensity values respectively, n is an empirically determined exponent, and $N_{pixels}$ is the number of pixels evaluated. The summation is taken over $N_{pixels}$ pixels. The brightness variation estimation can be calculated using all the pixels in a pair of successive frames or using the corresponding pixels within a selected region within the frames. Preferably, the pixel brightness variation processor is programmed to implement Eq. (1) such that the pixels between a pair of frames are compared, i.e., that the subscripts "old" and "new" distinguish a given pixel in one frame with the corresponding pixel in a succeeding frame. However, the processing might also be applied to pixels pairs from two scan lines within a single frame to estimate target motion even within a frame. In this case, if a change in motion is detected, then the imaging parameters could be updated before the frame acquisition is completed. This would result in a faster response to a change in target motion than would frame-to-frame processing.

Figure 4:
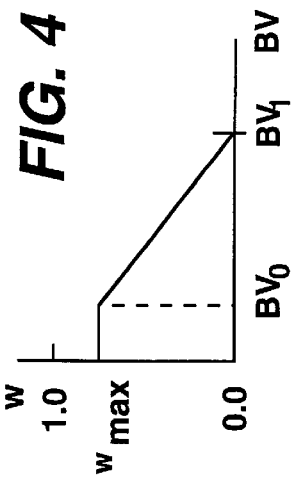
FIG. 4 is a graph showing a mapping from pixel brightness variation to frame-averaging gain which can be used in the preferred embodiment shown in FIG. 3.

The resulting BV value is input to a BV-to-frame-averaging-gain mapping 26, which preferably takes the form of a look-up table. One example of a BV-to-frame-averaging-gain mapping is depicted in FIG. 4, which shows a mapping in which the frame-averaging gain w decreases linearly from a maximum gain $w_{max} < 1$ to zero as BV increases from the value $BV_0$ to $BV_1$. The mapping shown in FIG. 4 can be constructed using the values $BV_0$, $BV_1$ and $w_{max}$ supplied by the system controller 14.

In response to input of the calculated BV value to the mapping 26, the corresponding gain w (or corresponding filter coefficients) is read from the look-up table and sent to the frame-averaging filter 8. In accordance with the preferred embodiment of the invention, the frame-averaging gain can be adjusted as a function of the current pixel brightness variation value.

In accordance with another preferred embodiment, the calculated BV values are sent to the system controller 14. The system controller is programmed to produce beamforming control parameters which are a function of the calculated BV value. Preferably, the number of transmit firings per frame is automatically adjusted as a function of the BV value. For example, over a range of target motion speeds, the number of transmit firings per frame can be reduced as the estimated target speed increases and can be increased as the estimated target speed decreases.

Alternatively, the target motion can be estimated by calculating the Doppler signal in a well-known manner. Conventional Doppler imaging produces one image from a sequence of transmit firings; typically a group of 5–15 firings are used for each scan line in the image. In accordance with an alternative preferred embodiment of the invention, a conventional Doppler processor 28 is utilized to calculate the Doppler signal for a subset of the scan lines in a frame. The target motion can be estimated from the Doppler signal by a processor 30.

Once the target motion is estimated, the frame rate must be controlled. Adjusting the frame-averaging may be straightforward, as shown in FIG. 4. Alternatively, an empirically determined nonlinear transform of the motion estimate might be required to control the degree of frame-averaging. The number of transmit firings can also be controlled. In its simplest implementation the number of transmit focal points would be reduced as the estimated target motion increases by eliminating some of the currently active transmit focal points. Conversely, the number of transmit focal points would be increased as the estimate target motion decreases by reactivating some focal points. For better performance, however, it would be desirable to also adjust the transmit aperture size the transmit excitation frequencies and the number of scan lines in an image frame as a function of the target motion estimate.

While the invention has been described with reference to preferred embodiments, it will be understood by those skilled in the art that various changes may be made and equivalents may be substituted for elements thereof without departing from the scope of the invention. For example, other techniques, such as frame-to-frame image cross-correlation, can be used to estimate target motion. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "acoustic data" refers to the data being processed in an ultrasound imaging system at any stage between the transducer and the display monitor. Specifically, the term "acoustic data" means, in the alternative, raw acoustic data entering the receiver from the transducer, pixel intensity data output by the detection and compression signal processor, grayscale imaging data output by the video processor, or the acquired data at any other stage in the beamforming, signal processing or scan conversion processes.

What is claimed is:

1. A method of operating an ultrasound imaging system in accordance with an imaging parameter, comprising the steps of:

acquiring acoustic data from a target by successively scanning the target with focused ultrasound wave energy;

estimating the target motion by applying a motion estimation algorithm to said acoustic data; and selecting a value of said imaging parameter as a function of said motion estimate.

2. The method as recited in claim 1, wherein said imaging parameter is the frame-averaging gain.

3. The method as recited in claim 1, wherein said imaging parameter is the number of transmit firings per frame.

4. The method as recited in claim 1, wherein said imaging parameter is the size of the transmit aperture.

5. The method as recited in claim 1, wherein said imaging parameter is the transmit excitation frequency.

6. The method as recited in claim 1, wherein said motion estimating step comprises the step of calculating a pixel brightness variation value.

7. The method as recited in claim 6, wherein said pixel brightness variation value is calculated using every pixel within the image.

8. The method as recited in claim 6, wherein said pixel brightness variation value is calculated using the pixels within a region in the image.

9. The method as recited in claim 6, wherein said pixel brightness variation value is calculated using the pixel values within a scan line or scan lines in the image.

10. The method as recited in claim 1, wherein said motion estimating step comprises the step of calculating a Doppler value.

11. An ultrasound imaging system comprising:

a beamformer (4) for acquiring acoustic data from a target by successively scanning the target with focused ultrasound wave energy;

a processor (24 or 30) for estimating the motion of the target by applying a motion estimation algorithm to said acoustic data;

a memory (26 or 32) storing a mapping for converting said motion estimate to a frame-averaging gain; and a frame-averaging filter (8) which frame-averages said acoustic data as a function of said frame-averaging gain.

12. The system as recited in claim 11, wherein said processor is programmed to calculate a pixel brightness variation value.

13. The system as recited in claim 11, wherein said processor is programmed to calculate a Doppler value.

14. The system as recited in claim 11, further comprising means (26) for constructing said mapping in said memory as a function of a maximum value of the frame-averaging gain, a minimum pixel brightness variation value and a maximum pixel brightness variation value.

15. The system as recited in claim 14, further comprising a system controller (14) programmed to provide said maximum frame-averaging gain value and said minimum and maximum pixel brightness variation values.

16. An ultrasound imaging system comprising:

a beamformer (4) for acquiring acoustic data from a target by successively scanning the target with focused ultrasound wave energy;

a beamformer controller (14) programmed to control said beamformer to transmit focused ultrasound wave energy and form receive beams in accordance with beamforming parameters; and a processor (24 or 30) for estimating the motion of the target by applying a motion estimation algorithm to said acoustic data, wherein said beamformer controller is further programmed to modify said beamforming parameters as a function of said motion estimate.

17. The system as recited in claim 16, wherein said beamforming parameters are modified to select the number of transmit firings in an image frame in response to a motion estimate.

18. The system as recited in claim 16, wherein said processor is programmed to calculate a pixel brightness variation value.

19. The system as recited in claim 16, wherein said processor is programmed to calculate a Doppler value.

20. An ultrasound imaging system comprising:

means (2, 4) for acquiring acoustic data from a target by successively scanning the target with focused ultrasound wave energy;

means (24 or 30) for estimating the motion of the target by applying a motion estimation algorithm to said acoustic data; and means (26 or 32) for selecting a value of an imaging parameter as a function of said motion estimate.

21. An imaging system comprising:

a transducer array (2) comprising a multiplicity of transducer elements for transmitting wave energy in response to electrical activation and converting returned wave energy into electrical signals;

a beamformer (4) for electrically activating said transducer elements to transmit focused wave energy and acquiring acoustic data from a target by beamforming said electrical signals from said transducer array into receive beams;

a display monitor (12) for displaying an image as a function of imaging data; and a computer (6, 8, 10, 14, 24 or 30, 26 or 32) programmed to perform the following steps:
  (a) controlling said beamformer to transmit focused ultrasound wave energy and form receive beams of data;
  (b) estimating the motion of a target by applying a motion estimation algorithm to received data;
  (c) determining a value of an imaging parameter as a function of said motion estimate;
  (d) processing subsequent data in accordance with said imaging parameter value to form imaging data; and
  (e) sending said imaging data to said display monitor.

22. The system as recited in claim 21, wherein said transducer elements are piezoelectric elements for transmitting ultrasound waves in response to electrical activation and converting returned ultrasound waves into electrical signals.

23. The system as recited in claim 21, wherein said imaging parameter is the frame-averaging gain.

24. The system as recited in claim 21, wherein said motion estimating step comprises the step of calculating a pixel brightness variation value.

25. The system as recited in claim 21, wherein said motion estimating step comprises the step of calculating a Doppler value.

26. The system as recited in claim 23, wherein said computer comprises memory (26 or 32) which stores a motion-to-frame-averaging gain mapping, said imaging parameter value selecting step comprising the step of reading a frame-averaging gain from said stored mapping.

* * * * *